US010179105B2

(12) United States Patent
De Kruif et al.

(10) Patent No.: US 10,179,105 B2
(45) Date of Patent: Jan. 15, 2019

(54) MICROGEL PARTICLES CONTAINING NANOTUBES LOADED WITH AN ACTIVE PHARMACEUTICAL INGREDIENT

(71) Applicant: Tillotts Pharma AG, Rheinfelden (CH)

(72) Inventors: Jan Kendall De Kruif, Saint Louis (FR); Carla Garofalo, Basel (CH); Gisela Ledergerber, Schenkon (CH); Martin Kuentz, Muttenz (CH); Roberto Carlos Bravo Gonzaléz, Binningen (CH); Felipe José Oliveira Varum, Basel (CH)

(73) Assignee: Tillotts Pharma AG, Rheinfelden (CH)

( * ) Notice: Subject to any disclaimer, the term of this patent is extended or adjusted under 35 U.S.C. 154(b) by 0 days.

(21) Appl. No.: 15/556,244

(22) PCT Filed: Mar. 21, 2016

(86) PCT No.: PCT/EP2016/056129
§ 371 (c)(1),
(2) Date: Sep. 6, 2017

(87) PCT Pub. No.: WO2016/162197
PCT Pub. Date: Oct. 13, 2016

(65) Prior Publication Data
US 2018/0049980 A1    Feb. 22, 2018

(30) Foreign Application Priority Data

Apr. 10, 2015    (EP) .................................... 15163193

(51) Int. Cl.
*A61K 9/50*    (2006.01)
*A61K 9/00*    (2006.01)
*A61K 38/00*   (2006.01)

(52) U.S. Cl.
CPC .......... *A61K 9/0092* (2013.01); *A61K 9/5036* (2013.01); *A61K 38/00* (2013.01)

(58) Field of Classification Search
CPC .. A61K 9/5031; A61K 9/5036; A61K 9/5042; A61K 9/5047; A61K 9/5052; A61K 9/5057
See application file for complete search history.

(56) References Cited

FOREIGN PATENT DOCUMENTS

| KR | 2011 0095590 | | 8/2011 |
| WO | 2012066507 | A2 * | 6/2008 |
| WO | WO 2008/066507 | | 6/2008 |

OTHER PUBLICATIONS

Liu, Mingxian et al., "Recent Advance in Research on Halloysite Nanotubes-Polymer Nanocomposite", *Progress in Polymer Science*, vol. 39 (8): 1498-1525 (Apr. 24, 2014).
Malmsten, Martin et al., "Microgels in Drug Delivery", *Microgel Suspensions*, Wiley VCH, Weinheim, Germnay, pp. 375-405, Jan. 14, 2011.

* cited by examiner

*Primary Examiner* — Carlos A Azpuru
(74) *Attorney, Agent, or Firm* — Chalin A. Smith; Smith Patent, LLC

(57) ABSTRACT

The present invention relates to microgel particles containing nanotubes loaded with an active pharmaceutical ingredient, a process for their preparation and a pharmaceutical composition comprising the same.

12 Claims, 3 Drawing Sheets

MICROGEL PARTICLES CONTAINING NANOTUBES LOADED WITH AN ACTIVE PHARMACEUTICAL INGREDIENT

PRIORITY

This application corresponds to the U.S. national phase of International Application No. PCT/EP2016/056129, filed Mar. 21, 2016, which, in turn, claims priority to European Patent Application No. 15/163193.4 filed Apr. 10, 2015, the contents of which are incorporated by reference herein in their entirety.

FIELD OF THE INVENTION

The present invention relates to microgel particles, a process for their preparation and a pharmaceutical composition comprising the same.

BACKGROUND OF THE PRESENT INVENTION

Oral delivery of active pharmaceutical ingredients (in the following abbreviated as API) is an important research field in pharmaceutical technology. On the way to the site of therapeutic activity for local-acting APIs as well as to the site of drug absorption for systemically exposed compounds, the bioavailability of APIs is compromised by several barriers. It starts with the luminal instability of a number of APIs in the harsh conditions of the gastro-intestinal tract, particularly in the stomach. Thus, a delivery system has to cope with acidic and enzymatic barrier to bring APIs intact to the site of absorption or of local action. Another substantial hurdle is the permeation step through the gut wall. In particular, large molecules are too bulky to be passively absorbed through the intestinal wall. Other ways of absorbing would have to be used such as paracellular transport, transcytosis or uptake by the intestinal M-cells. Some APIs have therapeutic action locally in the gastrointestinal lumen, in the mucosa, either binding to specific cell receptors or to cytokines produced by the epithelial cells. In these cases, the hurdles related to the systemic exposure through the gastrointestinal mucosa are of benefit for locally acting large molecules. In both events, i.e. systemically exposure or locally acting APIs, a common challenge is their delivery to the site of action without compromising their biological activity.

Among various options for protecting and delivering APIs to their site of action within the gastrointestinal tract after oral administration, a lipid-based drug delivery can be envisaged. However, a standard lipid based system is not able to target a specific region of the gut. Furthermore, one of the technical challenges is that an aqueous environment would be required for many APIs. A hydrophilic microenvironment might be obtained by inverse microemulsion or liposomes. A basic issue of using liposomes or W/O microemulsions is that upon dilution in the gastrointestinal tract, there are phase changes taking place leading to colloidal instability. Moreover, these lipid-based formulations are digested by the lipophilic enzymes including the phospholipase A2, which degrades liposomes and other phospholipid-based systems. Therefore, a more stable hydrophilic compartment would be desirable for drug inclusion.

One option for including an API in a hydrophilic compartment is microencapsulation. Many different techniques for the production of microspheres and microcapsules have been described. An overview over these techniques is provided by M. Whelehan, et al., in Journal of Microencapsulation, 2011; 28(8): 669-688. The vibrating nozzle technique is a widely used method for the production of microspheres and microcapsules. This technique is for example disclosed in WO 2009/130225 and by M. Homar, et al., in Journal of Microencapsulation, February 2007; 24(1): 72-81, C.-Y. Yu, et al., in Journal of Microencapsulation, 2010; 27(2): 171-177, H. Brandenberger, et al., in Journal of Biotechnology 63 (1998) 73-80 and G. Auriemma, et al., in Carbohydrate Polymers 92 (2013) 367-373.

Microspheres and microcapsules obtained by the known methods contain the API encapsulated within a gel. Such gels can be stable even under the harsh chemical conditions for example in the stomach and therefore can protect the API for a certain period of time until the gel is degraded and the API is released. However, degradation of the gel can be fast and it can be difficult to tailor the release of the API in a desired manner. Furthermore, gels often provide only little protection against enzymatic digestion.

As another drug delivery system the use of nanotubes has been proposed (Price R. R., et al., J. Microencapsulation 2001; 18(6): 713-22). Nanotubes showed the capacity of storing APIs in their lumen or to adsorb compounds on their surface. Both luminal and surface additions and modifications have been proposed to increase the loading efficiency of the tubes or to modify the release properties of this system.

Many of these modifications were reviewed by Liu M., et al., Prog. Polym. Sci. 2014; 39(8): 1498-525. However, the release of API from nanotubes is generally fast and nanotubes loaded with APIs also do not provide adequate protection of the API for example against enzymatic digestion.

Therefore, there is still a need for further improved drug delivery systems which overcome the above problems. In particular, there is a need for drug delivery systems which effectively protect the API against enzymatic digestion, in particular against enzymatic digestion along the gastrointestinal tract, which can be easily prepared with standard techniques and which allow tailoring the release profile of the API from a pharmaceutical preparation containing the drug delivery system after administration.

SUMMARY OF THE INVENTION

It has now surprisingly been found that the above problems can be solved by incorporating nanotubes loaded with an API into microgel particles. The present inventors found that there is a synergistic interaction between the gel-forming polymer of the microgel particles and the nanotubes which results in a surprising increase in the protection of the API from enzymatic digestion. Furthermore, it was found that the interaction between the gel-forming polymer of the microgel particles and the nanotubes results in a certain release of the API which can be tailored for providing microgel particles exhibiting a desired release profile.

Thus, the present invention relates to microgel particles containing nanotubes loaded with an active pharmaceutical ingredient.

In the context of the present invention "microgel particles" denote microparticles formed of a gel (microgels). The microgel particles are preferably such which are obtainable by the vibrating nozzle technique (also called "prilling").

The microgel particles of the present invention are suitable for delivering an API to its site of pharmacological action or absorption upon oral administration. Thereby the microgel particles protect the API for example against enzymatic digestion/degradation and the polymer in the microgel particles can for example be selected such that it provides mucoadhesion in order to further facilitate the local action or systemic absorption of the API.

The API contained in the microgel particles is not limited to specific physiochemical properties. The API can be hydrophilic or hydrophobic. However, if the microgel particles are prepared using an aqueous solution of a polymer, hydrophilic APIs are preferred. The microgel particles can contain one or more APIs either in pure form or for example in the form of vesicles containing the API. The microgel particles of the present invention are particularly suitable for bulky API molecules which are otherwise difficult to be transported to their sites of pharmacological action upon oral administration. In particular for bulky API molecules it is difficult to maintain a favorable environment during their transport through the gastrointestinal tract in order to preserve their biological activity. This problem is successfully solved by the present invention.

A further advantage is that for the preparation of the microgel particles mild conditions are applied. The API remains in liquid form, no temperature-dependent process is involved and very low shear forces are applied.

Furthermore, pharmaceutical proteins and peptides are becoming an important class of therapeutic drugs. However, due to their large molecular weight and size, they show poor permeability characteristics through various mucosal surfaces and biological membranes. Moreover, their inherent chemical and physical instability are also factors which result in the low bioavailability associated with the oral delivery. A further advantage of the microgel particles of the present invention is that since the microgel particles usually provide a hydrophilic environment proteins and peptides which are usually also hydrophilic, can be loaded in and onto nanotubes and then easily be dissolved in the microgel particles, thus being readily available at target site. Furthermore, the microgel particles can successfully protect peptides and proteins from the gastrointestinal tract environment. Therefore, proteins and peptides are preferred APIs in the microgel particles of the present invention.

The microgel particles can be in the form of beads containing the gelled polymer throughout the particles forming a matrix for the nanotubes or in the form of microcapsules comprising a core containing the nanotubes and a shell formed of the gelled polymer.

The microgel particles can have any suitable size. The size of the particles can for example be in the range of 1 to 2.000 µm, preferably 10 to 2.000 µm or 20 to 2.000 µm, more preferably in the range of 50 to 1.000 µm, and even more preferably in the range of 80 to 500 µm. In one embodiment the particle size distribution expressed by the 90th percentiles $D_{90}$ can be below 1000 µm, such as below 700 µm and preferably below 500 µm. Preferably, the particle size distribution $D_{90}$ is above 10 µm, more preferably above 20 µm. The particle size distribution $D_{90}$ can be in the range of 10 to 1000 µm, preferably in the range of 100 to 700 µm and more preferably in the range of 250 to 500 µm. In another embodiment the particle size distribution expressed by the median particle size $D_{50}$ can be below 1.000 µm, such as below 700 µm and preferably below 500 µm. Preferably, the median particle size $D_{50}$ can be above 10 µm, more preferably above 20 µm. The median particle size $D_{50}$ can be in the range of 10 to 1.000 µm, preferably in the range of 100 to 700 µm and more preferably in the range of 250 to 500 µm. In a preferred embodiment the particle size distribution satisfies both criteria, the above $D_{90}$ values and the above $D_{50}$ values.

Furthermore, the microgel particles can have any suitable form. For example, the particles can be spherical or non-spherical, like elliptic. Furthermore, the particles may exhibit a toroidal shape which resembles that of erythrocytes. The particle shape can be described by the elongation factor, which is the max Feret diameter (the linear segment connecting the two perimeter points that are the furthest apart) divided by the Feret equivalent rectangular short side (the shortest side of the rectangle with the same area as the particle and the longest side equal in length to the max Feret diameter). Preferably, the elongation factor of the particles is in the range of 1.27 to 2.60, more preferably in the range of 1.27 to 2.30, and even more preferably in the range of 1.60 to 2.20.

The above described size and form of the microgel particles can be observed using an Olympus CKX41SF microscope equipped with an Olympus SC30 digital camera. Pictures are taken at different magnification to visually inspect the shape of the particles. The particle size and shape of the microgels are assessed by dynamic image analysis with the XPT-C (PS-Prozesstechnik GmbH, Basel, Switzerland). The microgels are kept in suspension in their hardening bath, and then flowed (n=1000) in front of a near-infrared light source. The particle size is expressed by the Waddle disk diameter, which is the diameter of a disc with the same area as the detected particle.

Besides the nanotubes loaded with the API, the microgel particles contain a polymer and preferably a gelling agent. The polymer must be gelled in order to effectively protect the API against the environment in the gastrointestinal tract. Suitable gel-forming polymers are for example chitosan, chitosan derivatives, polyacrylic acids, alginate, carrageenan, gum Arabic, gellan gum, proteins, xanthan gum, gelatin, agar, pectin, hyaluronic acid and its salts. These polymers can be used alone or in combination of two or more of these polymers.

Suitable chitosan derivatives are alkylated and/or carboxyalkylated and/or PEGylated chitosans wherein the hydroxyl and/or amino groups, preferably the amino groups may be partially or totally alkylated and/or carboxyalkylated. Suitable hydrocarbon groups in the alkylated and/or carboxyalkylated chitosans are saturated, unsaturated or aromatic hydrocarbon groups, such as alkyl or alkenyl groups, in particular those having 1 to 24, preferably 1 to 10, more preferably 1 to 6 carbon atoms. As aromatic hydrocarbon group phenyl is suitable. The hydrocarbon groups may be substituted with one or more substituents, such as hydroxyl, amino and carboxy. A preferred alkyl group is methyl and a preferred carboxyalkyl group is carboxymethyl. Other suitable residues are for example phthalate, succinate and fatty acid esters, such as linoleate and oleate. As chitosan derivatives N-trimethyl chitosan and carboxymethyl chitosan (mono-N-carboxymethylated chitosan) can be exemplified. As proteins albumin and whey proteins can be exemplified. A preferred gel-forming polymer is carboxymethyl chitosan.

Gelling of the polymer is preferably obtained in the presence of a divalent and/or trivalent metal ion as gelling agent. For example, sodium alginate gels in the presence of divalent or trivalent metal ions, such as $Ca^{2+}$, due to the formation of Ca-alginate.

Suitable divalent metal ions are for example $Ca^{2+}$, $Mg^{2+}$, $Zn^{2+}$, $Ba^{2+}$ and $Cu^{2+}$. A suitable trivalent metal ion is for example $Al^{3+}$. $Ca^{2+}$, $Mg^{2+}$ and $Zn^{2+}$ are preferred and $Ca^{2+}$ being most preferred. Other suitable gelling agents are for example tripolyphosphate, citric acid, phytic acid and glutaraldehyde. Mixtures of two or more of these ions or substances may also be used. The ions are provided in the liquid non-aqueous, in particular lipid composition by dissolving suitable salts (or for example their hydrates) in the composition, for example $CaCl_2$ or one of its hydrates, such as $CaCl_2$ dihydrate.

Some polymers can be gelled for example by differences in ionic strength, temperature or pH. In these cases it is not necessary that the microgel particles contain a gelling agent.

The microgel particles may contain further ingredients, such as water, glycerol, buffering agents and the like.

The microgel particles contain nanotubes loaded with the API. Any known nanotubes are suitable, although pharmaceutically acceptable nanotubes are preferred. Examples for suitable nanotubes are carbon, boron nitride, titanium dioxide, metal sulfide, metal halogenide and aluminosilicate nanotubes. As metal sulfide nanotubes molybdenum, tungsten and copper sulfide nanotubes are known. As metal halogenide nanotubes nickel chloride, cadmium chloride and cadmium iodide nanotubes are known.

In a preferred embodiment of the present invention, the nanotubes are aluminosilicate nanotubes, in particular Halloysite nanotubes. Halloysite is a two-layered aluminosilicate of the chemical formula $Al_2Si_2O_5(OH)_4 2H_2O$.

Commercially available aluminosilicate and in particular Halloysite nanotubes can have rather small inner lumen diameter. It can therefore be advantageous to increase the inner lumen diameter of the nanotubes by alkaline or acidic etching in order to allow the loading of the lumen with macromolecules like peptides or to increase the loading capacity of the nanotubes.

Alkaline or acidic etching of the nanotubes, such as aluminosilicate nanotubes can be conducted as described by E. Abdullayev et al., ACS NANO, 2012: 6 (8) 7216-26. For example the nanotubes can be etched using an aqueous solution of an acid, such as sulfuric acid, or a base, such as sodium hydroxide. The concentration of the acid or base can be selected by the skilled person according to the requirements and can be, for example, in the range of 0.1-3 M, such as 0.5, 1.0 or 2.0 M. Etching can be conducted by dispersing the nanotubes in the acidic or alkaline solution for a time sufficient to obtain the desired lumen increase. The time depends on the acid or base used, its concentration and the temperature of the dispersion. The temperature can be for example between room temperature and the boiling point of the dispersion, preferably between 30 and 90° C., more preferably between 40 and 70° C. The time can range from 5 minutes to 10 hours, such as from 5 minutes to 120 minutes, preferably from 10 minutes to 60 minutes. When the desired degree of etching is obtained the etched nanotubes are separated from the dispersion for example by filtration or centrifugation. Subsequently, the etched nanotubes can be washed and dried.

Furthermore, it has surprisingly been found that alkaline or acidic etched nanotubes are particularly suitable to protect APIs from enzymatic digestion and exhibit strong specific interaction with the gel forming the microgel particles. Therefore, in a particularly preferred embodiment of the present invention the microgel particles contain alkaline or acidic etched nanotubes, preferably alkaline or acidic etched aluminosilicate nanotubes, more preferably alkaline or acidic etched Halloysite nanotubes.

The size of the nanotubes is not particularly limited and can be selected according to the requirements. In one embodiment of the present invention, the nanotubes can have an average length of from 0.1 to 15 μm, preferably of from 0.1 to 10 μm, more preferably from 0.1 to 1 μm, such as for example from 100 to 700 nm. The average external diameter of the nanotubes can for example be in the range of 20 to 100 nm, preferably from 20 to 70 nm, more preferably from 20 to 40 nm. The average lumen diameter depends on the average external diameter of the nanotubes and in any case must be smaller than the average external diameter. Suitable average lumen diameters for example range from 3 to 90 nm, preferably from 3 to 50 nm, more preferably from 3 to 30 nm, such as from 5 to 25 nm.

Loading of the nanoparticles with the API can be conducted by techniques known to the skilled person. For example, the nanotubes can be suspended in a solution of the API followed by centrifugation, removing the supernatant and drying of the thus obtained samples.

The present invention further relates to a process of preparing the above described multi-particulate drug delivery system. This process comprises the steps of
 a) providing a mixture of a gel-forming polymer and nanotubes loaded with an active pharmaceutical ingredient,
 b) forming the mixture obtained in step a) into microdroplets,
 c) gelling the microdroplets obtained in step b) in a liquid composition to form microgel particles.

In step a) of the above process, the gel-forming polymer and the nanotubes loaded with active pharmaceutical ingredient are mixed. Generally, this mixing is carried out in the presence of water to form a solution of the gel-forming polymer. The amount of the gel-forming polymer is not particularly limited and it depends on the viscosity of the obtained solution. If the viscosity becomes high, it will be difficult to form the mixture into microdroplets. Therefore, low viscosity solutions are preferred. For example, when carboxymethyl chitosan is used as gel-forming polymer, the solution can advantageously contain 1 to 8 wt. %, preferably 2 to 6 wt. %, most preferably about 4 wt. % of the gel-forming polymer, each based on the total weight of the obtained mixture. The solution can also contain a mixture of two or more gel-forming polymers.

The mixture can comprise further ingredients, such as glycerol. The amount of glycerol can be for example in the range of 1 to 70 wt. %, preferably in the range of 20 to 70 wt. %, more preferably in the range of 30 to 60 wt. % and most preferably in the range of 40 to 55 wt. % based on the total weight of the mixture.

In a further preferred embodiment the mixture additionally contains one or more buffering agents such as Tris (tris(hydroxymethyl)aminomethane) or PBS (phosphate buffer saline).

In step b) of the above process, the mixture obtained in step a) is formed into microdroplets. Formation of microdroplets can be carried out by any method known to the person skilled in the art. Various methods are for example described in M. Whelehan, et al., in Journal of Microencapsulation, 2011; 28(8): 669-688. Mechanical techniques are the most common types of mechanisms used for producing microparticles for medical applications. They are based on the principle of generating a droplet from a polymeric solution extruded through a nozzle and work using mechanical means (i.e. cutting or vibration forces) to increase the normal dripping process at the orifice, or they break up the extruded liquid stream produced by the polymer when it is passed through the nozzle. Some of the main mechanical technologies for forming a fluid dispersion into droplets and subsequent conversion into gel particles are: coaxial airflow, electrostatic extrusion, rotating disc, jet-cutting, spray-drying, vibrating nozzle and prilling. All these methods are known to a person skilled in the art and suitable devices are commercially available. In the process of the present invention step b) preferably is carried out by using vibrating nozzle technique or prilling.

In step c) of the above process, the microdroplets obtained in step b) are gelled to form microgel particles. Generally, after production, the droplets are immediately solidified to microgel particles (spheres or capsules) by chemical means using a gelling agent, such as chemical cross-linking (e.g. chitosan with glutaraldehyde), coacervation/precipitation (e.g. mixtures of chitosan, gellan, carrageenan using physicochemical properties like transition temperature or pH) or ionic gelation (e.g. chitosan or alginate and divalent or trivalent metal ions). Ionic gelation is preferred in the process of the present invention.

The gelling in step c) is carried out in a liquid composition. The liquid composition can be aqueous or non-aqueous. For example, the liquid composition can comprise an alcohol such as ethanol, diethylene glycol monoethyl ether (DEGEE) and/or water. The liquid composition may additionally comprise a gelling agent such as the salt of a divalent or a trivalent metal ion. Further possible ingredients are fillers and co-solvents.

In one embodiment, the process of the present invention further comprises the step of separating the microgel particles from the liquid composition and optionally drying the thereby obtained microgel particles. Separation and drying can be conducted by usual methods, such as filtration, centrifugation, drying at slightly elevated temperatures, optionally under reduced pressure, or lyophilization. Between the separation and the drying step, the obtained microgel particles can be washed, for example with water and/or ethanol.

The microgel particles of the present invention can be used as pharmaceutical composition or for the preparation of a pharmaceutical composition. The pharmaceutical composition can be for oral administration, for example in the form of a suspension or syrup. Preferably, the microgel particles are, however, further processed to obtain a suitable unit dosage form, such as capsules. Suitable pharmaceutical capsules are for example hard or soft shell capsules. Suitable capsule materials are for example gelatine, hydroxypropyl methylcellulose and starch.

DETAILED DESCRIPTION OF THE PREFERRED EMBODIMENTS

The invention will now be further illustrated by the examples which are not intended to be construed as being limiting.

Example 1

Luminal Etching of Nanotubes

Halloysite nanotubes (HNT) were purchased from Sigma-Aldrich Chemie GmbH (Buchs, Switzerland). The HNT internal lumen diameter was enlarged by alkaline chemical etching by suspending HNT in a 2 M solution of sodium hydroxide in a ratio of 1:10. The dispersion was sonicated for 50 minutes at 50° C. The HNT samples were centrifugated at 4000 rpm for 15 minutes. Then, the supernatant was removed and 40 ml of demineralized water were added. Subsequently, both centrifugation and washing steps were repeated three times using phosphate buffer Salin (PBS) at pH 6.8 instead of demineralized water. A final centrifugation and washing step was repeated with demineralized water. The base-modified HNT (bHNT) was desiccated at 105° C. until no weight variation could be detected. Both, base-modified HNT (bHNT) and non-treated HNT (nHNT) were used in the further experiments.

Loading with BSH

For loading the HNT with bovine serum albumin (BSA) as model API 1 g of dried HNT was added to 1 ml of BSA solution at a concentration of 10% (w/v). The sample was mixed for 5 minutes on IKA® Vortex Genius 3 (Huber & Co. AG, Rheinach, Switzerland). Subsequently, the sample was put in a vacuum chamber at room temperature for 1 minute at 100 mbar. This step was repeated twice to remove air in the suspension and from the nanotube lumen. The suspension was then centrifugated for 10 minutes at 4000 rpm. After removing the supernatant, fresh aliquot of BSA solution with identical concentration was added, and the loading process repeated to ensure highest loading efficiency. Once the supernatant was removed again, the sample was dried at 40° C. for about 20 hours in a vacuum oven.

Figure 1B:
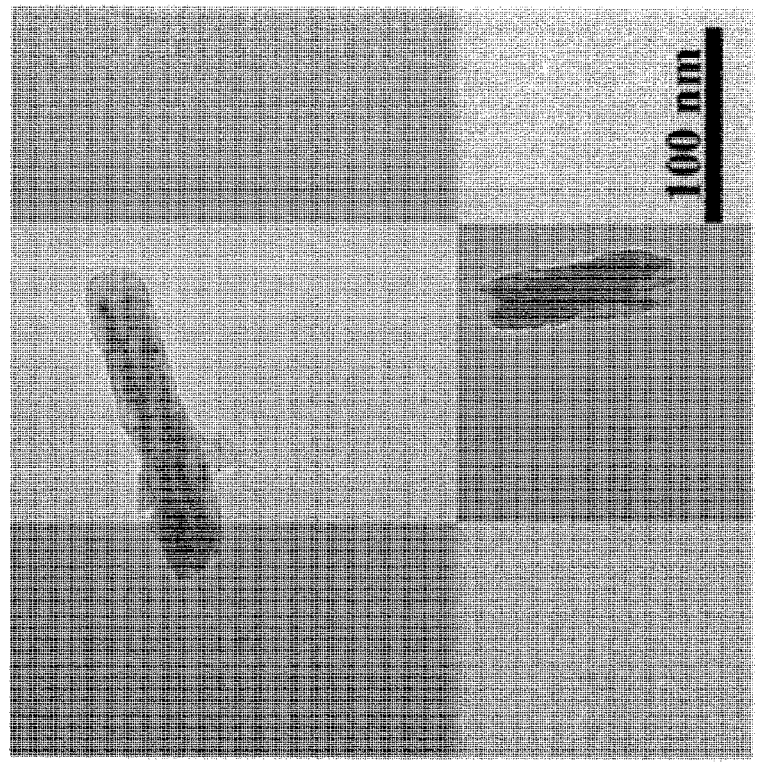
FIGS. 1A and 1B show transmission electron microscope pictures of Halloysite nanotubes (1A) and BSA-loaded Halloysite nanotubes (1B). Scale bar is 200 nm.
Figure 1A:
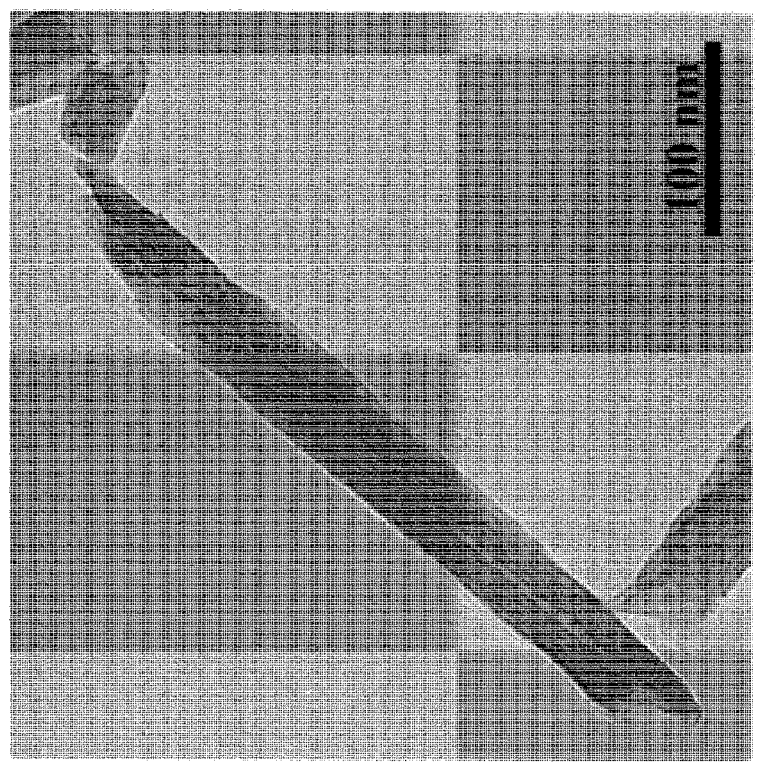

Transmission electron microscope pictures of HNT and BSA-loaded HNT are shown in FIGS. 1A and 1B.

Formation of NiMOS by Prilling

Prilling was carried out on an Encapsulator Biotech from EncapBioSystem AG (Greifensee, Switzerland). A polymeric solution containing 4% (w/v; dry weight) of mono-N-carboxymethyl chitosan (MCC) was prepared in PBS pH 6.8. The solution was stirred overnight to allow complete dissolution and hydration of the MCC polymeric chains. Subsequently, the solution was vacuum filtered through a Whatman® GF/D glass microfiber filter (GE Healthcare AG, Glattbrugg, Switzerland). The BSA-loaded HNT, both non-treated and base-modified, were added to the polymeric solution (ratio 1:20). The system was then thoroughly mixed for 30 minutes and sieved through a 125 μm mesh stainless steel sieve to separate HNT clusters. Three different hardening bath compositions were chosen to collect the droplets falling from the prilling device, namely ethanol, DEGEE, and water. Calcium chloride anhydrous was added up to 4% (w/w) concentration in the hardening baths and these were stirred until complete dissolution of the salt. Tween® 80 was also added in the aqueous solution to a 2% (w/w) concentration to reduce its surface tension, according to the Encapsulator Biotech instructions.

An Omnifix® syringe (B. Braun Melsungen AG, Melsungen, Germany) was filled with HNT-loaded polymeric solution and then attached to the prilling device. This solution was pumped through a 300 μm nozzle with a 12.5 ml min$^{-1}$ flow rate. The vibration was set to a 1240 Hz frequency and to an amplitude of 9. The droplet stream passed through the electrode ring charged with 2500 V. The droplets were collected after a ~13 cm fall into a grounded beaker containing 75 ml of hardening bath. A total quantity of 5 g of polymeric solution was prilled for each batch. The HNT-containing microgels were left in the hardening baths for 30 minutes. The microgels loaded with nHNT were named under the term nNiMOS, whereas those containing bHNT were called bNiMOS. "Blank" microgels, i.e., without HNT but still loaded with BSA, were produced with the same settings.

NiMOS and blank microgels were filtered through a 125 µm mesh stainless steel sieve. All the microgels were then washed with water, ethanol, and water again. The microgel batches were dried in a glass oven B-585 (Büchi Labortechnik AG) at 40° C. for 3 hours in 20 mbar vacuum, at a rotation speed of 20 rpm. The microgels were stored in sealed vials at 4° C.

Figure 2A:
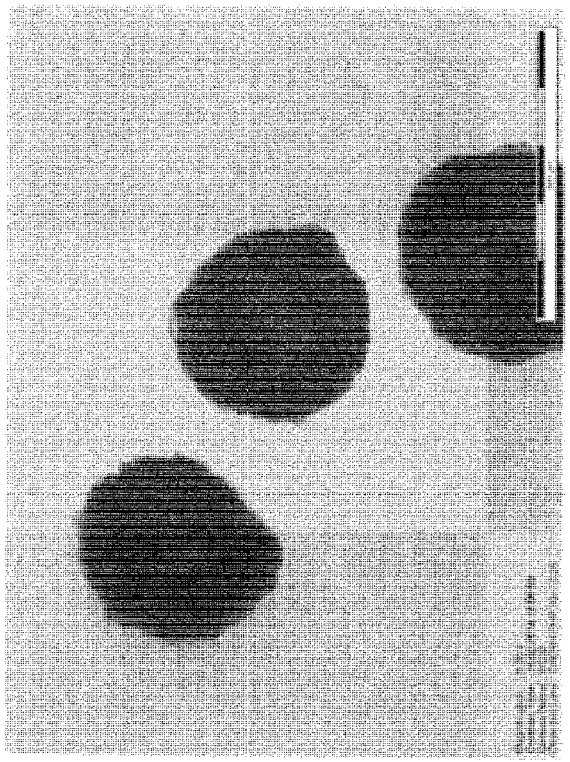
FIGS. 2A and 2B show optical microscope pictures of microgel particles according to the invention formed in ethanol (2A) and diethylene glycol monomethyl ether (2B). Scale bar is 1 mm.
Figure 2B:
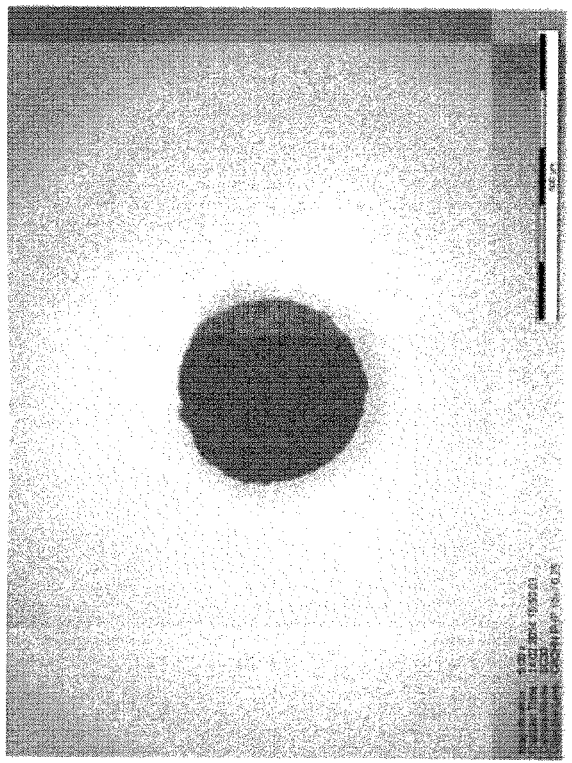

NiMOS formed in ethanol and DEGEE are shown in FIGS. 2A and 2B.

Example 2

A BSA release test was carried out on bHNT, on the blank microgels containing BSH without nanotubes, and on different bNiMOS. These samples were transferred into 15 mL Cellstar® tubes (Greiner Bio-One GmbH, Frickenhausen, Germany) and 10 mL of PBS pH 6.8 were added as dissolution medium. Each sample was repeated 6 times. The test tubes were laid horizontally in a Multitron Standard shaking incubator (Infors AG, Bottmingen, Switzerland), incubated at 37.0° C. and shaken at 200 rpm. Aliquots of 100 µL were drawn at selected time points (5, 10, 15, 30, 45, 60, 75, 90, 105, 120, 150, 180, and 210 minutes). A final aliquot was taken after 24 hours at equilibrium. After each withdrawal, the sample taken was replaced with 100 µL of fresh medium. The samples were centrifuged for 10 minutes at 14 000 rpm. The protein content was assessed with the Micro BCA® Protein Assay Kit according to the manufacturer's instructions.

Figure 3:
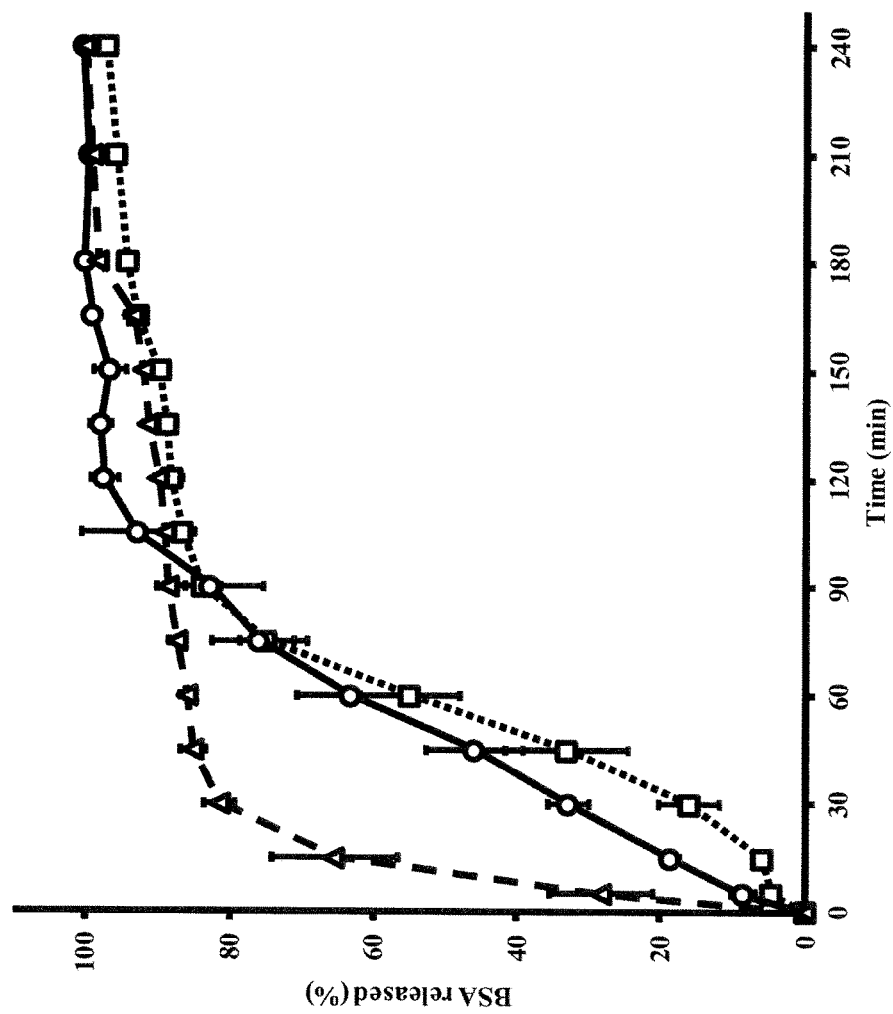
FIG. 3 shows the release profiles of BSA from microgel particles without nanotubes (circles and continuous line; not according to the invention); from Halloysite nanotubes (triangles and long dashes; not according to the invention); and microgel particles containing BSA loaded nanotubes (squares and dotted line, according to the invention).

The release profiles are shown in FIG. 3. It can be seen that from blank microgels the BSA is released slowly until about 90% of the BAS is released. During this time the microgels displayed nearly zero order release kinetics. Then, after 105 minutes, a plateau state was reached. For the BSA-loaded HNT the samples released their content rapidly (>80% in 30 minutes) and then only gradually reached a plateau. Surprisingly, a different behavior was observed for the BSA release from bNiMOS. These microgel particles which are according to the invention showed a sigmoidal release profile of BSA. A brief initial lag phase occurred for the first fifteen minutes. Subsequently, the BSA was released almost linearly until 85% after 120 minutes. Finally, the profiles stabilized to match that of the BSA-loaded bHNT. The differences in the release profiles demonstrate a strong interaction between the API loaded nanotubes and the microgels.

Example 3

The ability of the microgel particles according to the invention to protect the API against enzymatic digestion was tested.

To simulate the enzymatic digestion, the microgels were incubated in PBS pH 6.8 containing trypsin (5 mg mL$^{-1}$) at 37° C. in a Multitron Standard shaking incubator (Infors AG) with an agitation of 200 rpm. The enzymatic digestion was then halted after one hour by adding trypsin inhibitor (5 mg mL$^{-1}$). The complete release of BSA was allowed over a 4-hour period at the same temperature and shaking. To evaluate the trypsin activity, negative controls were prepared by adding the trypsin inhibitor at the beginning of the enzymatic digestion. The samples were then evaluated by means of sodium dodecyl sulfate gel electrophoresis (SDS-PAGE).

The results of this test are summarized in Table 1.

TABLE 1

Comparison of protein stability enzymatic digestion. Significance expressed as *($p < 0.001$), ($p < 0.01$), and *($p < 0.05$) after ANOVA testing. Data are expressed as mean value ± standard deviation (n = 3).

| Stability | BSA-loaded microgel | nHNT | bHNT | nNiMOS | bNiMOS | Significance |
|---|---|---|---|---|---|---|
| SDS-PAGE | | | | | | |
| Protection from digestion (%) | 4.85 ± 4.38 | 45.99 ± 6.99 | 56.53 ± 6.98 | 62.22 ± 9.64 | 81.54 ± 3.76 | *** |

The BSA-loaded microgels showed poor protection of the protein. The protection against trypsin digestion was below 5%. The use of non-treated and base-modified HNT considerably increased the protection to 46% and 56%, respectively. However, by forming NiMOS with the nHNT 62% of BSA remained unscathed. Finally, the luminal etching of Halloysite nanotubes combined with microencapsulation, i.e. bNiMOS, demonstrated protection from enzymatic digestion to a highest value of 82%. The differences between these values were found to be statistically significant after ANOVA testing.

The invention claimed is:

1. Microgel particles containing nanotubes loaded with an active pharmaceutical ingredient, wherein the nanotubes are alkaline or acidic etched aluminosilicate nanotubes.

2. The microgel particles according to claim 1, wherein said particles contain at least one gel-forming polymer selected from the group consisting of chitosan, chitosan derivatives, polyacrylic acids, alginate, carrageenan, gum Arabic, gellan gum, xanthan gum, proteins, gelatin, agar, pectin and hyaluronic acid or a salt thereof.

3. The microgel particles according to claim 2, wherein the gel-forming polymer is gelled in the presence of a divalent and/or trivalent metal ion.

4. The microgel particles according to claim 1, wherein the nanotubes are Halloysite nanotubes.

5. The microgel particles according to claim 1, wherein the nanotubes have an average length of from 0.1 to 15 µm and an average external diameter of 20 to 100 nm.

6. The microgel particles according to claim 1, wherein the nanotubes have an average lumen diameter of from 3 to 40 nm.

7. The microgel particles according to claim 1, wherein said particles have a particle size distribution $D_{90}$ of below 1000 µm.

8. A process for the preparation of the microgel particles according to claim 1, said process comprising the steps of
   a) providing a mixture of a gel-forming polymer and nanotubes loaded with an active pharmaceutical ingredient,
   b) forming the mixture obtained in step a) into microdroplets,
   c) gelling the microdroplets obtained in step b) in a liquid composition to form microgel particles.

9. The process according to claim 8, wherein step b) is carried out by using vibrating nozzle technique or prilling.

10. The process according to claim 8, comprising the further step of separating the microgel particles from the liquid composition.

11. Microgel particles obtained by the process according to claim 8.

12. A pharmaceutical composition comprising the microgel particles according to claim 1.

* * * * *